United States Patent [19]

Barrick

[11] Patent Number: 5,772,594

[45] Date of Patent: Jun. 30, 1998

[54] FLUOROSCOPIC IMAGE GUIDED ORTHOPAEDIC SURGERY SYSTEM WITH INTRAOPERATIVE REGISTRATION

[76] Inventor: Earl F. Barrick, 8904 Gallant Green Dr., McLean, Va. 22102

[21] Appl. No.: 731,504

[22] Filed: Oct. 16, 1996

Related U.S. Application Data

[60] Provisional application No. 60/005,331 Oct. 17, 1995.

[51] Int. Cl.⁶ ........................................ A61B 5/05
[52] U.S. Cl. ..................... 600/407; 606/130; 378/20; 378/205
[58] Field of Search .................. 128/653.1; 606/130; 378/20, 205, 207, 206; 600/407

[56] References Cited

U.S. PATENT DOCUMENTS

| | | |
|---|---|---|
| 4,037,592 | 7/1977 | Kronner . |
| 4,403,321 | 9/1983 | DiMarco . |
| 4,418,422 | 11/1983 | Richter et al. . |
| 4,485,815 | 12/1984 | Amplatz et al. . |
| 4,621,628 | 11/1986 | Brudermann . |
| 4,625,718 | 12/1986 | Olerud et al. . |
| 4,791,934 | 12/1988 | Brunnett ............................ 128/653 |
| 4,803,976 | 2/1989 | Frigg et al. . |
| 5,013,317 | 5/1991 | Cole et al. . |
| 5,178,621 | 1/1993 | Cook et al. . |
| 5,309,913 | 5/1994 | Kormos et al. .................. 128/653.1 |
| 5,320,111 | 6/1994 | Livingston ....................... 128/754 |
| 5,383,454 | 1/1995 | Buckolz . |
| 5,408,409 | 4/1995 | Glassman et al. ............... 364/413.13 |
| 5,427,097 | 6/1995 | Depp ................................ 128/653.1 |
| 5,446,548 | 8/1995 | Gerig et al. ..................... 356/375 |
| 5,478,341 | 12/1995 | Cook et al. . |
| 5,478,343 | 12/1995 | Ritter . |
| 5,622,170 | 4/1997 | Schulz ............................ 128/653.1 |
| 5,638,819 | 6/1997 | Manwaring et al. ............ 128/653.1 |
| 5,690,108 | 11/1997 | Chakeres ........................ 128/653.1 |

FOREIGN PATENT DOCUMENTS

| | | |
|---|---|---|
| 964149 | 3/1975 | Canada . |
| 350996 | 1/1990 | European Pat. Off. . |
| 3042343 | 6/1982 | Germany . |
| WO 9103982 | 4/1991 | WIPO . |

OTHER PUBLICATIONS

Bouazza–Marouf et al.; "Robotic–Assisted Internal Fixation of Femoral Fractures", IMECHE, pp. 51–58 (1995).

*Primary Examiner*—Marvin M. Lateef
*Assistant Examiner*—Eleni Mantis Mercader
*Attorney, Agent, or Firm*—James Creighton Wray; Meera P. Narasimhan

[57] ABSTRACT

The present invention is an improved system for allowing an orthopaedic surgeon to safely determine the precise trajectory of insertion of a guide pin or screw into an object bone and to check the accuracy of the procedure using real time feedback. The system uses a C-arm fluoroscope in conjunction with a three-dimensional optical digitizer to provide a real time image of the drill and object bone on a screen. The system uses light emitting diodes (LEDs) positioned on the C-arm fluoroscope and on the drill and two dimensional image registration of the object bone to orientate the surgeon. In addition, LEDs are attached to a reference bar positioned on the object bone. The distinctive pattern formed by the combination of these elements allows the surgeon to continually observe the progress of the surgery without necessitating additional x-ray images. A computer software program allows the surgeon to record the position of the object bone, to correct the parallax of the C-arm fluoroscope and to relate the position of the object bone in the two fields by two dimensional image registration to determine the exact relative position of the object bone seen on the two images.

9 Claims, 3 Drawing Sheets

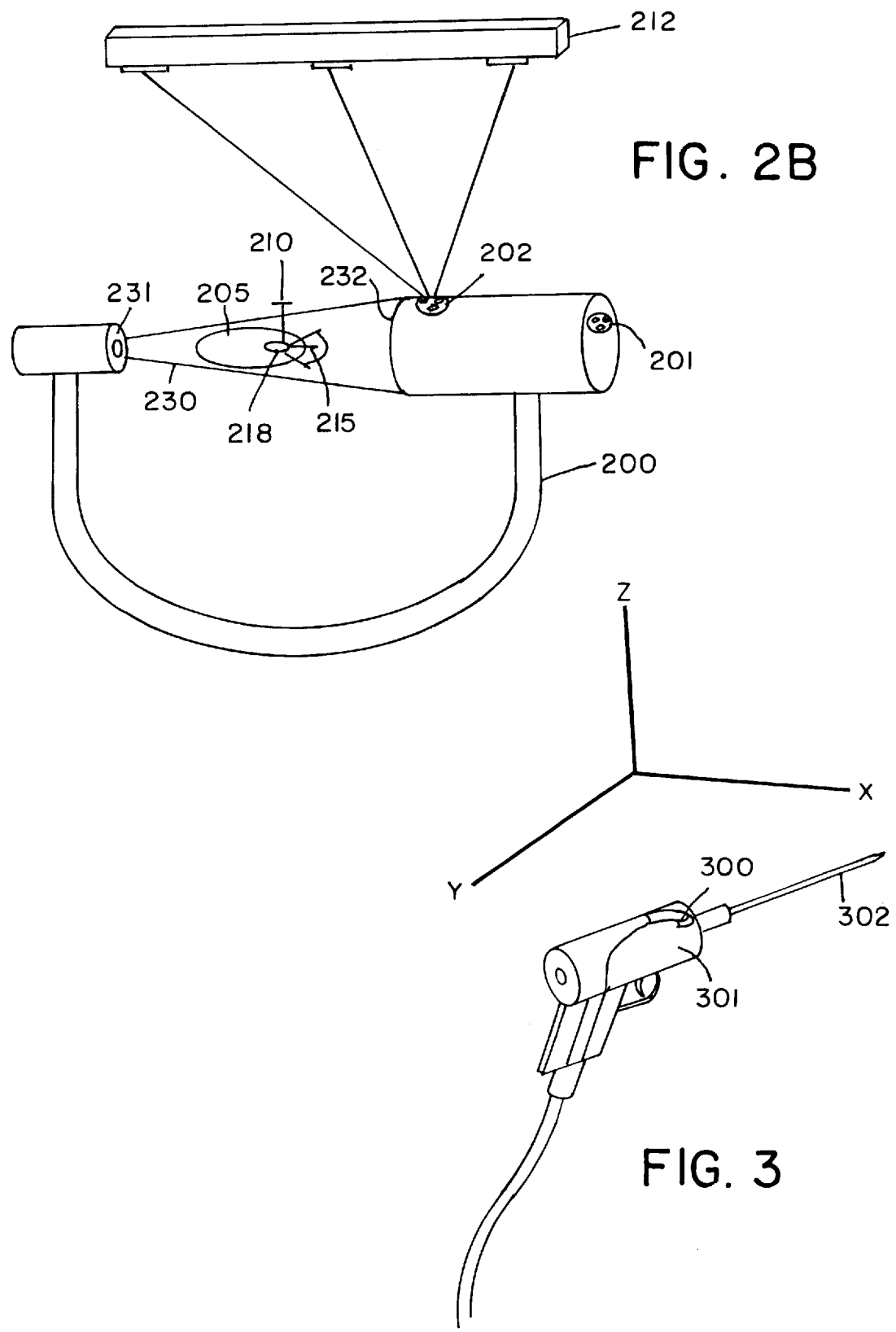

FLUOROSCOPIC IMAGE GUIDED ORTHOPAEDIC SURGERY SYSTEM WITH INTRAOPERATIVE REGISTRATION

BACKGROUND OF THE INVENTION

This application claims the benefit of U.S. Provisional Application Ser. No. 60/005,331, filed Oct. 17, 1995.

The present invention relates to systems for image guided surgery, and in particular to a fluoroscopic image guided orthopaedic surgery system with intraoperative registration.

In orthopaedic surgery it is often necessary to insert a guide pin or screw into an object bone at a predetermined trajectory. Pre-operative planning depends on two-dimensional radiographic images which typically consists of two views taken at approximately right angles to one another. From those two views it is possible to determine the shape and structure of a long bone. Using that method, the path of insertion for a guide pin or screw can be accurately determined. However, in practice the actual aiming of a guide pin or drill bit is an inaccurate art, as the object bone is often seen only at one surface or is not seen at all and therefore positioning of the guide pin or drill bit depends on fluoroscopic visualization. That method is also time consuming as the C-arm images must be taken separately and the drapes must be rearranged each time an image is taken. As bony tissue is unyielding, the track of the pin or drill bit is determined by the angular approach determined before entering the object bone. That angular approach is difficult to determine under normal circumstances and often multiple attempts are needed as feedback is gradually obtained from fluoroscopic images. Existing methods of calculating the proper angle of guide pin insertion for hip pinning involve placing data manually into a computer program, which in turn outputs an angle of guide pin insertion.

Radiation exposure is a necessary part of any procedure for calculating the proper angle of guide pin or screw insertion. Radiation exposure is considered to be a hazard. Ionizing radiation has no safe, threshold of exposure below which it ceases to have adverse effects although an arbitrary level is assumed. There has been a recent upward revision of risk estimates of radiation exposure, but absolute levels of safe exposure remain unknown. Exposure to the surgical team as well as the patient during orthopaedic procedures using fluoroscopy is a universal concern. Consequently, a reduction in the amount of radiation exposure is highly desirable.

Operative stereotactic localization using either frames or three dimensional digitizers is currently being used in neurosurgery and otolaryngology. Those methods require the use of computed axial tomography (x-ray photographs of a selected plane in the body) or magnetic resonance imaging ("MRI") prior to surgery. They also involve placing markers on the scalp prior to the imaging study of the head. The markers must be left in the same position until surgery is performed to confirm intraoperative registration. Such imaging studies are routinely performed for most intracranial procedures but are impractical for most orthopaedic procedures, especially those involving long bones. A probe marked with light emitting diodes ("LEDs") or other digitizing emitters is used to localize those markers or pins using a three dimensional digitizing device at the time of surgery. A disadvantage of that system is that images are normally obtained hours before use; thus, the images used are not up to date (real time) and are often not reflective of the current position of the object bone.

Registration markers cannot be used on the outside of the body in most orthopaedic cases as the skin does not adhere to the. underlying bone. Pre-operative registration for robotic placement on the femoral component for total hip arthroplasty requires the use of a separate procedure to insert pins for such markers. Such a separate procedure is highly impractical for routine orthopaedic procedures.

An alternative method of registration for image guided surgery requires wide operative exposure, such as in pedicle screw insertion in spine surgery. The various fiducials are determined by touching prominent or distinctive anatomic points with a digitizing probe employing the stereotactic localization system. Furthermore, the system also requires a preoperative computed axial tomography.

SUMMARY OF THE INVENTION

The present invention allows an orthopaedic surgeon to safely determine the precise trajectory of insertion of a guide pin or screw into an object bone and to check the accuracy of the procedure using real time feedback.

The present invention remedies the disadvantages of prior art systems by providing a safe and reliable system for determining the precise trajectory for insertion of a guide pin or screw into an object bone and checking the accuracy of the procedure using real time feedback.

A three-dimensional optical digitizer is used to determine the position in six degrees of freedom of a portable fluoroscopy machine ("C-arm fluoroscope") and the object region of the skeleton. Light emitting diodes ("LEDs") are placed in distinctive patterns on the C-arm fluoroscope and attached to the bone. The LEDs are attached to the bone with a percutaneous screw device, such as a reference bar. A computer program records those positions in relation to an optical position sensor.

X-rays are then taken by the C-arm fluoroscope with the two positions of the tubes being approximately at right angles to one another. The optical position sensor then determines where the C-arm fluoroscope is positioned in relation to the LED markers attached to the reference bar which is connected to the object section of the skeleton and to the C-arm fluoroscope. The exact position is determined by using two dimensional image registration, matching the outline of the bone in two planes. If necessary, inserting three or more distinctly shaped radiopaque markers are inserted into the bone at different sites. These fiducial markers are attached to threaded tipped guide pins inserted percutaneously. Thus, the object portion of the skeleton is localized in six degrees of freedom by the optical digitizer.

The present invention prevents the problem of parallax. Parallax is the disproportional enlargement of a bone when it is recorded on an image receiving screen. The computer corrects for the parallax of the x-ray machine and results in magnification of the objective by calculating two fields of the x-ray positions.

The computer program relates the position of the object bone with or without fiducial markers in the two fields to determine the exact relative position of the object bone seen on the two images. Once those two images are displayed on the monitor, no further x-rays are needed. That results in a substantial reduction in the amount oft ionizing radiation used. The images displayed are those familiar to the surgeon but with the usual distortion eliminated.

A drill, with attached LEDs, inserts the guide pin or drill bit in the bone in a position the surgeon chooses based on the supplied information. The three-dimensional optical digitizer determines the position of the drill in relation to the optical digitizer camera and the object section of the skeleton with its fiducials. A graphic display of the guide pin or drill bit of predetermined length is then overlaid on the images of the object bone in near real time. Thus, the position of the inserted pin or drill bit is adjustable immediately.

If desired, a final pair of x-rays are taken to check the position of the guide pin or drill bit in the object bone. Furthermore, should some change in position occur during surgery, registration is updated during the procedure by repeating the two fluoroscopic x-ray views with the C-arm fluoroscope. As a result, the method of registration for image guided surgery in the present invention is not dependent on otherwise unneeded imaging studies done prior to surgery.

A preferred responsive fluoroscopic image guided surgery system for inserting a guide pin or screw into an object bone at a predetermined trajectory comprises a drill for inserting the guide pin or screw into the object bone, an x-ray generator, an x-ray receiver for receiving the x-ray beam emitted from the x-ray generator and for generating a radiographic image. A first set of emitters positioned on the x-ray receiver, and a second set of emitters positioned on the drill. Radiopaque markers may be arranged on the object bone.

Preferably a percutaneous screw device is positioned on the object bone, a third set of emitters is positioned on the percutaneous screw attached to the bone, a sensor is provided for sensing signals emitted by the emitters and for generating a digitized image. A display is provided which displays the radiographic image and the digitized image.

Preferably, the radiopaque markers are three dissimilar distinctively shaped radiopaque markers and the percutaneous screw has a referenced bar attached to it.

In preferred embodiments, plural multiple-threaded tipped guide pins are provided for percutaneously inserting the radiopaque markers into the object bone.

Preferably, the emitters are digitizing emitters and the sensor is an optical position sensor. The digitizing emitters are light emitting diodes and the optical position sensor is an optical digitizer camera.

In preferred embodiments, the x-ray generator and the x-ray receiver comprise a C-arm fluoroscope. Preferably, the x-ray generator produces an enlarging beam for increasing an apparent size of the object bone on the display.

Preferably, the first set of emitters further comprise lateral emitters positioned on a side of the x-ray receiver and anteroposterior emitters positioned on a top of the x-ray receiver.

In preferred embodiments, a computer program corrects a parallax of the radiographic image caused by increase in the apparent size of the object bone on the display.

In preferred embodiments, the radiopaque markers are positioned in a distinctive pattern on the object bone and the first, the second and the third set of emitters are positioned in a distinctive pattern for providing a relative orientation of the object bone and the drill on the monitor.

A preferred responsive fluoroscopic image guided surgery system for use in orthopaedic surgery comprises a C-arm fluoroscope for generating radiographic images, a first set of digitizing emitters positioned on the C-arm fluoroscope, a guide pin, a drill for inserting the guide pin in a surgeon-chosen position in an object bone, a second set of digitizing emitters positioned on the drill, a reference bar positioned in the object bone, a third set of emitters positioned on the reference bar, an optical position sensor for sensing signals emitted by the digitizing emitters, multiple distinctly shaped radiopaque markers, multiple-threaded tipped guide pins for percutaneously inserting the radiopaque markers into the object bone, a computer connected to the sensor for receiving and converting the signals and for generating a graphic image of the object bone, and a monitor for displaying radiographic images of the object bone produced by the C-arm fluoroscope and graphic images produced by the optical position sensor indicating a position of the digitizing emitters overlaying the radiographic images in near real time for continually monitoring a position of the guide pin being inserted.

Preferably, the first set of emitters, the second set of emitters and the third set of emitters are light emitting diodes and the optical position sensor is an optical digitizing camera.

Preferably, the first set of emitters, the second set of emitters and the third set of emitters are placed in a distinctive pattern for providing a relative orientation of the object bone and the drill on the monitor.

Preferably, the multiple radiopaque markers are three radiopaque markers each having a different shape and wherein the radiopaque markers are positioned in a distinctive pattern on the object bone.

In preferred embodiments, the guide pin is a drill bit of predetermined length.

A preferred method of determining a precise trajectory for the insertion of a screw into a bone comprises the steps of providing a C-arm fluoroscope, light emitting diodes ("LEDs"), dissimilar distinctively shaped radiopaque markers, an optical position sensor, a drill, and a guide pin, positioning a first set of LEDs on the C-arm fluoroscope, positioning a second set of LEDs on a percutaneous screw mounted on the bone, positioning a third set of LEDs on the drill, positioning the radiopaque markers at different sites on the bone with multiple-threaded tipped guide pins, taking a first x-ray of the bone with the C-arm fluoroscope in a first position, taking a second x-ray of the bone with the C-arm fluoroscope in a second position, displaying the first and the second x-rays on a monitor screen, correcting for parallax caused by the C-arm fluoroscope, recording positions of the LEDs with the optical position sensor, converting the positions of the LEDs to produce at least two graphic images of the bone, overlaying the graphic images on the radiographic images, using the images to relate the position of the fiducials in the two fields to determine the exact relative position of the bone seen on the two images, inserting the guide pin into the bone in a desired position using the drill, displaying graphically the guide pin overlaid on the images of the bone in near real time and adjusting the position of the inserted pin.

Preferably, the step of taking the second x-ray comprises taking the second x-ray of the bone approximately at right angles to the first x-ray of the bone.

Preferably, the step of inserting a guide pin further comprises the steps of inserting a drill bit in a desired position in the bone with the drill.

Preferably, the steps of checking for a change in position of the object bone comprises taking a third and a fourth x-rays with the C-arm fluoroscope, registering corresponding updated images on the monitor and adjusting a position of the inserted pin immediately.

Preferably, the step of converting the positions of the LEDs to produce two graphic images of the bone comprises converting by a computer.

These and further and other objects and features of the invention are apparent in the disclosure, which includes the above and ongoing written specification, with the claims and drawings.

BRIEF DESCRIPTION OF THE DRAWINGS

FIGS. 2A and 2B are perspective illustrations of the intraoperative setting showing the C-arm fluoroscope, an optical digitizer camera and the object body.

FIG. 3 is an illustration of a drill with mounted light emitting diodes which schematically shows orthographic axes.

DETAILED DESCRIPTION OF PREFERRED EMBODIMENTS

Figure 1A:
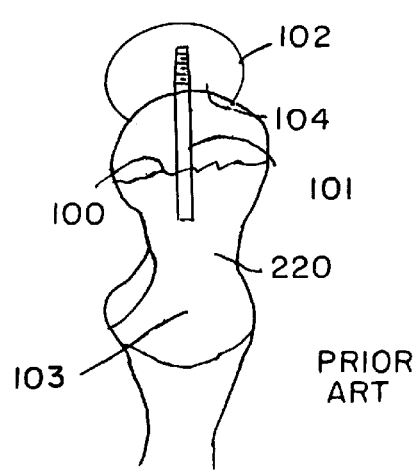
FIGS. 1A and 1B are illustrations of an anterior view and a lateral view of a proximal femur having an intertrochanteric fracture with a hip screw in an optimal position.
Figure 1B:
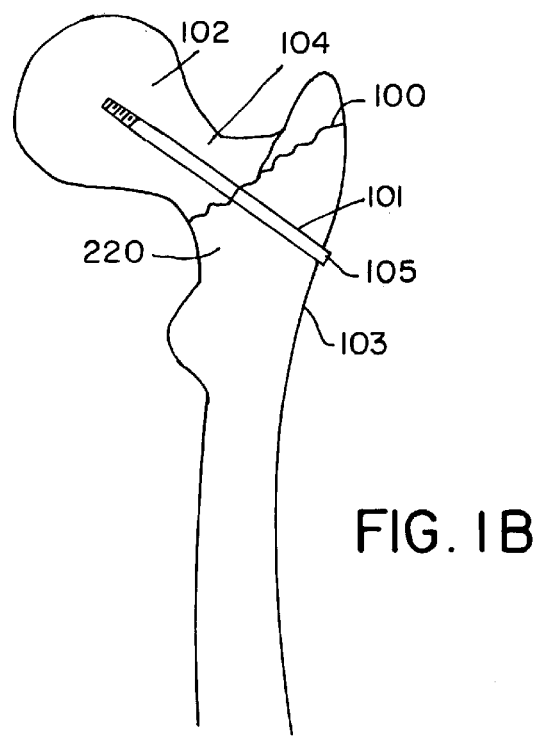

Referring to FIG. 1, an operation for the internal fixation of an intertrochanteric hip fracture 100 requires a guide pin and subsequently a cannulated screw 101 to be placed into a femoral head 102 from a lateral cortex 103 of a proximal femur 220 via a femoral neck 104. The guide pin determines the position of the cannulated screw 101. The ideal position of the guide pin and thus the screw 101 is entirely within the femur 220. An end of the pin and subsequently an end 105 of the screw 101 is best positioned near a subcortical bone but should not penetrate the cortex 103. The best results of an intertrochanteric fracture 100 has been shown to occur when a large cannulated screw 101 is used in a center of an end at the subcortical bone. Using prior art methods, that position is typically obtained by placing the guide pin by estimation and by following its course on entry with repeated x-ray views in two planes. Those two planes necessitate moving the C-arm fluoroscope 200 (see FIG. 2A) from a first position to a second position 90 degrees from the first position. Repeated movement along the planes, as desired, provides optimal positioning. Using image guided surgery of the present invention, operating time and radiation exposure are reduced. The accuracy and thus long-term results of this type of surgery are improved.

Figure 2A:
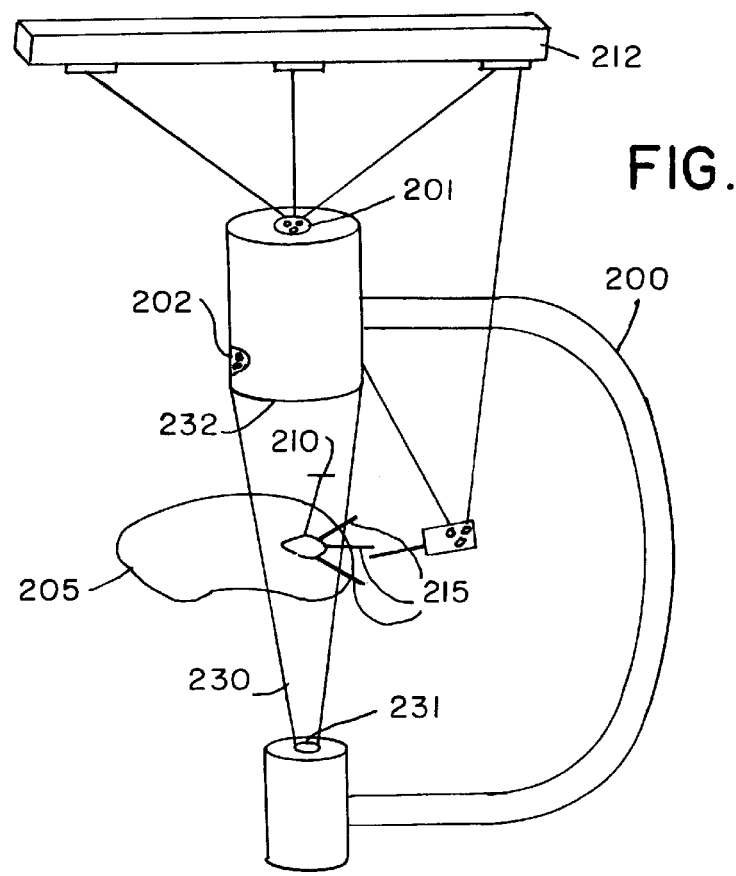

FIGS. 2A and 2B show the new system for fluoroscopic image-guided orthopaedic surgery with intraoperative registration. Light emitting diodes (LEDs) 201, 202, are attached to a portable C-arm fluoroscope 200 at two sites. A first LED 201 is placed on the C-arm fluoroscope 200 to determine the position of the C-arm fluoroscope 200 when it is in the upright position as in FIG. 2A. FIG. 2A shows an anteroposterior x-ray view of a patient 205 in a supine position. A second LED 202 is located so that it is seen by an optical digitizer camera 212 when the C-arm fluoroscope 200 is in a horizontal position as in FIG. 2B. FIG. 2B corresponds to am lateral x-ray view.

The patient 205 lies supine in traction on a fracture table during the procedure. After appropriate sterile preparation, a reference bar 210 is inserted through a small incision into ilium 218. Optical digitizer software is programmed to recognize the region of the skeleton attached to the reference bar 210 as a rigid body. A rigid body computer model thus remains immobile and other objects with attached LEDs move in relation to that rigid body. The femur must remain immobile in relation to the ilium 218 which is usually the case.

When the C-arm fluoroscope 200 is in the horizontal position as shown in FIG. 2B, the second LED 202 faces the optical digitizer camera 212 and indicates again where the C-arm fluoroscope 200 is, in three dimensional space, when in that position. The computer calculates exactly where the body 205 and the femur 220 seen on the x-ray are in relation to the optical digitizer camera 212. That calculation is possible with fiducial pins 215 and the femur 220 now being recorded in two positions. The position of the intersecting planes of each fiducial marker 216 indicate with great accuracy exactly where the femur 220 is in relation to the camera 212.

Figure 4B:
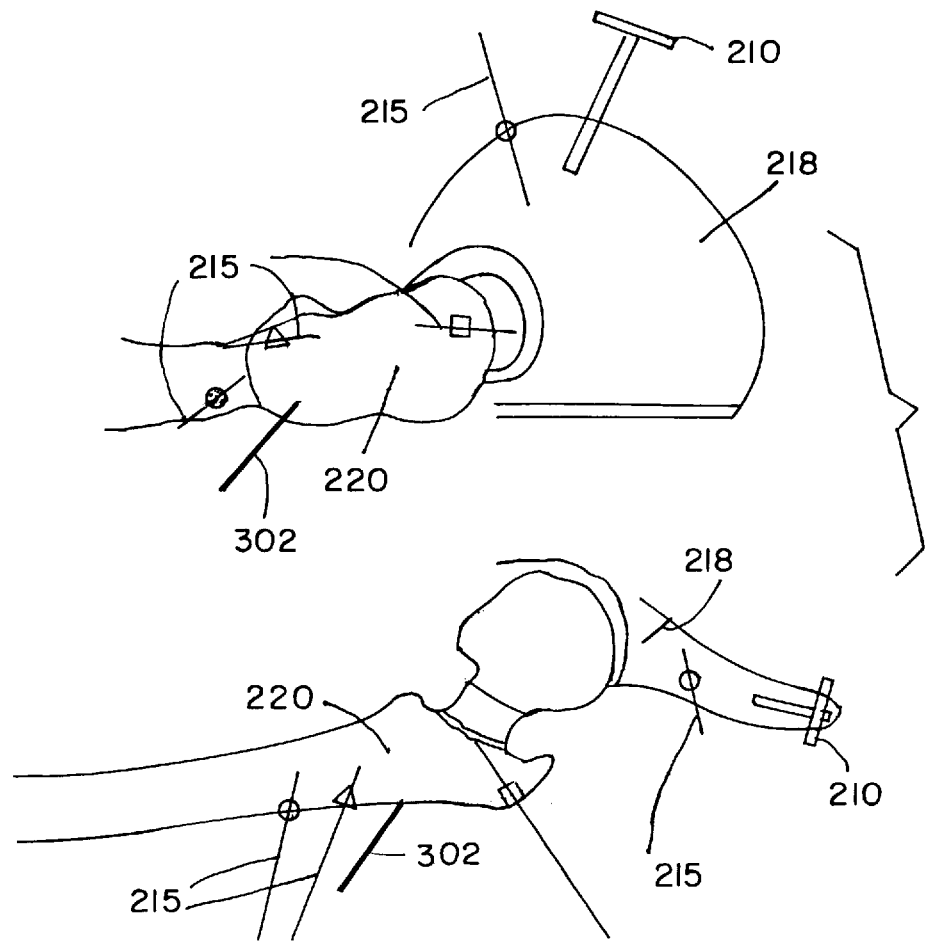
FIG. 4B is an illustration of a computer monitor screen having two radiographic images of the object bone taken at positions approximately 90 degrees from one another in which the radiopaque markers and a reference bar are positioned on the object bone.

Third LEDs 300 are mounted on a body of a drill 301 as show in FIG. 3. Emitted signals are received by the optical digitizer camera 212 when it is placed in an operating field. The computer then determines the position of the drill 301 relative to the reference bar 210 and thus to the femur 220. A graphic image of a guide pin 302 is displayed on the monitor screen 400 as seen in FIG. 4B to show the relationship of the guide pin 302 to the femur 220 in both the anteroposterior and the lateral views. The guide pin 302 is inserted in the femur 220 in the desired position using image guidance.

Figure 4A:
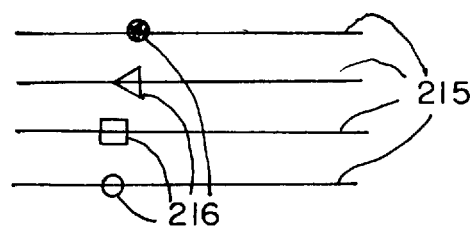
FIG. 4A is an illustration of threaded tip guide pins having various distinctly shaped radiopaque markers.

Pins 215 are illustrated in FIGS. 4A and 4B in more details. FIG. 4B illustrates the x-ray views seen with the C-arm fluoroscope 200. The proximal femur 220 is exposed through a routine lateral incision. Three or more threaded fiducial pins 215 with dissimilar distinctively shaped radiopaque markers 216 are then inserted at different sites in the proximal femur 220.

X-rays at approximate right angles are then taken in the standard anteroposterior and lateral views. An x-ray beam 230 is broadcast in a widening band from a source 231. That results in the image of the object femur 220 being enlarged when it is recorded on an image receiving screen 232 creating a phenomenon called parallax. The size of the image as seen on a monitor screen 400 can be corrected once the two positions of the C-arm fluoroscope 200 have been determined as described above. The distance of the femur 220 in relation to the source 231 and a receiving screen 232 in one position is determined by the three dimensional position of the femur 220 determined by the other position.

When the C-arm fluoroscope 200 is in the upright position ash seen in FIG. 2A, the first LED 201 faces the optical digitizer camera 212 and indicates to the computer where the C-arm fluoroscope 200 is, in three dimensional space. Thus, the computer calculates the plane in which the body of the patient 205 lies, in relation to the reference bar 210.

If the reference bar 210 is moved or loosened, registration is done again during the operation just by repeating the two x-ray views. Once reference pins 215 are in place, further identification of fiducials by the tedious method of touching points with a probe are unnecessary. Therefore, the accuracy of the guide pin 302 insertion is much greater than with current methods.

While the invention has been described with reference to specific embodiments, modifications and variations of the invention may be construed without departing from the scope of the invention, which is defined in the following claims.

I claim:

1. A responsive fluoroscopic image guided surgery system for inserting a guide pin or screw into an object bone at a predetermined trajectory comprising a drill for inserting the guide pin or screw into the object bone, an x-ray generator, an x-ray receiver for receiving an x-ray beam emitted from the x-ray generator and a fluoroscopic imager for generating a two-dimensional radiographic image, radiopaque markers positioned with respect to the object bone, a first set of emitters positioned on the x-ray receiver, a second set of emitters positioned on the drill, a sensor for sensing signals emitted by the emitters and for generating a digitized image, a display for displaying the radiographic image and the digitized image, and a computer programmed to match the two-dimensional radiographic images thereby effecting two-dimensional image registration.

2. The system of claim 1, wherein the x-ray generator and the x-ray receiver comprise a C-arm fluoroscope.

3. The system of claim 2, further comprising a computer program for correcting a parallax of the radiographic image caused by increase in the apparent size of the object bone on the display by the C-arm fluoroscope.

4. The system of claim 1, wherein the radiopaque markers are positioned in a distinctive pattern on the object bone and wherein the first and the second set of emitters are positioned in a distinctive pattern for providing a relative orientation of the object bone and the drill on the monitor.

5. A responsive fluoroscopic image guided surgery system for use in orthopaedic surgery comprising a C-arm fluoroscope for generating radiographic images, a first set of emitters positioned on the C-arm fluoroscope, a guide pin or a drill bit, a drill for inserting the guide pin or drill bit in a surgeon-chosen position in an object bone, a second set of emitters positioned on the drill, an optical position sensor for sensing signals emitted by the emitters, multiple distinctly shaped radiopaque markers positioned with respect to the object bone, a computer connected to the sensor for receiving and converting the signals and for generating graphic images of the object bone and the guide pin or drill bit, and a monitor for displaying the images of the object bone produced by the C-arm fluoroscope and the images produced by the optical position sensor indicating a position of the guide pin or drill bit overlaying the images in near real time for continually monitoring a position of the guide pin or drill bit being inserted.

6. The system of claim 5, wherein the first set of emitters and the second set of emitters are placed in a distinctive pattern for providing a relative orientation of the object bone and the drill on the monitor.

7. A method of determining a precise trajectory for the insertion of a screw into a bone comprising the steps of providing a C-arm fluoroscope, light emitting diodes ("LEDs"), dissimilar distinctively shaped radiopaque markers, a position sensor, a drill, and a guide pin or drill bit, positioning a first set of LEDs on the C-arm fluoroscope, positioning a second set of LEDs on the drill, positioning the radiopaque markers at different sites with respect to the bone, taking x-rays of the bone with the C-arm fluoroscope in plural positions, displaying images of the x-rays on a monitor screen, correcting for parallax caused by the C-arm fluoroscope, recording positions of the LEDs with the position sensor, converting the positions of the LEDs to produce at least two graphic images of the bone, overlaying the graphic images on the radiographic images, using the images to relate the position of the bone in the two fields to determine the exact relative position of the bone seen on the two images, inserting the guide pin or drill bit into the bone in a desired position using the drill, displaying graphically the guide pin or drill bit overlaid on the images of the bone in near real time and adjusting the position of the inserted guide pin or drill bit.

8. The method of claim 7, wherein the converting the positions of the LEDs to produce two graphic images of the bone comprises converting by a computer.

9. The system of claim 5, wherein the computer is programmed to match images from the fluoroscope to effect two-dimensional image registration.

\* \* \* \* \*